(12) United States Patent
Eppley

(10) Patent No.: US 6,187,044 B1
(45) Date of Patent: Feb. 13, 2001

(54) IMPLANT FILLER MATERIALS AND METHODS COMPRISING NONIONIC SURFACTANTS

(75) Inventor: Barry L. Eppley, Danville, IN (US)

(73) Assignee: Advanced Research and Technology Institute, Inc., Indianapolis, IN (US)

(*) Notice: Under 35 U.S.C. 154(b), the term of this patent shall be extended for 0 days.

(21) Appl. No.: 09/003,724

(22) Filed: Jan. 7, 1998

(51) Int. Cl.⁷ .............................. A61F 2/12; A61F 2/04; A61K 47/00
(52) U.S. Cl. .......................... 623/8; 516/198; 424/70.31; 623/23.71
(58) Field of Search ................... 623/8, 7, 1, 2, 623/3; 424/898, 70.31; 516/198

(56) References Cited

U.S. PATENT DOCUMENTS

| | | | |
|---|---|---|---|
| 3,934,274 | * | 1/1976 | Hartley, Jr. . |
| 4,650,487 | * | 3/1987 | Chaglassian ............................. 623/8 |
| 4,731,081 | * | 3/1988 | Tiffany et al. .......................... 623/8 |
| 4,775,379 | | 10/1988 | Fogarty et al. . |
| 4,778,832 | * | 10/1988 | Futami et al. . |
| 5,067,965 | | 11/1991 | Ersek et al. . |
| 5,215,541 | * | 6/1993 | Nashef et al. .......................... 623/2 |
| 5,549,672 | | 8/1996 | Maddock et al. . |
| 5,658,329 | | 8/1997 | Purkait . |
| 5,834,026 | * | 11/1998 | Lu ....................................... 424/498 |

OTHER PUBLICATIONS

Eppley et al., "A Potential Material Composite for Dermal and Subcutaneous Augmentation", Ann. Plast. Surg. vol. 34, pp. 463–468, 1994.*

Rheingold et al., *Plastic and Reconstructive Surgery,* vol. 93, No. , *Experience with 326 Inflatable Breast Implants* (Jan. 1994) pp. 118–122.

Young et al., *Plastic and Reconstructive Surgery,* vol. 88, No. 3, *Biocompatibility of Radiolucent Breast Implants* (Sep. 1991) pp. 462–474.

Beisang et al., *Plastic and Reconstructive Surgery,* vol. 87, No. 5, *Radiolucent Prosthetic Gel* (May 1991) pp. 885–892.

Lin et al., *Plastic and Reconstructive Surgery,*vol. 94, No. 2, *Hyaluronic Acid–Filled Mammary Implants: An Experimental Study,* (Aug. 1994) pp. 306–315.

* cited by examiner

Primary Examiner—David H. Willse
Assistant Examiner—Choon P. Koh
(74) Attorney, Agent, or Firm—Leydig, Voit & Mayer, Ltd.

(57) ABSTRACT

Compositions and methods are disclosed for filling prostheses for implantation into human soft tissue. The compositions comprise at least one nonionic surfactant, such as a polysorbate, which can be provided to fill a physiologically compatible shell or containment sac of the prosthesis. The liquid compositions of the present invention have a relatively high viscosity and are quickly absorbed from body tissues, metabolized and excreted with no known adverse effect. The compositions can be injected into the physiologically compatible shell either before, during or after the surgical implantation procedure.

22 Claims, No Drawings

IMPLANT FILLER MATERIALS AND METHODS COMPRISING NONIONIC SURFACTANTS

BACKGROUND OF THE INVENTION

The present invention relates generally to filler materials for implantable prostheses for use in plastic and reconstructive surgery, as might be particularly useful in breast reconstruction and augmentation.

Subcutaneous reconstructive implant procedures for augmenting or reconstructing certain soft tissues in humans, including breast and facial implants, have been in wide use since at least the early 1960s. The implants consist of hollow, physiological shells filled with a filler material. The physiological shells are typically formed from silicone rubber or other elastic biocompatible materials which have enough memory to preserve a desired shape. In order to minimize the risk of leakage, the physiological shell often consists of multiple layers.

Controversy has surrounded the materials used to fill the physiological shells. One filling material that was previously quite popular was silicone gel. However, the use of silicone gel is associated with a number of problems. For example, silicone gel is not sufficiently radiolucent and can thus obscure mammographic signs of breast cancer. In fact, some researchers have suggested that breast implants containing silicone gel fillers prevent early detection of breast cancer and hence reduce the probability of a promising prognosis once cancer is detected. Because an estimated one in nine women will develop breast cancer, and, with cancer recurring in another 1 in 3, the risk of delay of detection caused by silicone gel implants is quite significant. Another problem with silicone gel fillers is that the body is unable to metabolize or excrete the silicone gel. In the event of a leak from the shell, the silicone gel is apt to migrate or leak into surrounding tissue where an undesirable body reaction can ensue, thereby requiring surgical removal or other treatment.

In recent years, saline has supplanted silicone gels as the most prevalent implant filler material. However, saline is also ill-suited for use as an implant filler material. Significantly, saline has a relatively low viscosity and is a poor lubricant thereby resulting in an excessively soft implant that is prone to rippling, fold flaws and spontaneous deflation. Saline fillers also suffer from an unnatural "feel." In the event of containment sac perforation, filler escape is immediate with spontaneous deflation. Further, if air enters the containment sac during filling, a postoperative audible noise may result.

Other previous approaches have involved the use of soybean oil, hyaluronic acid and polyethylene glycol. However, the long-term safety and stability of these materials has yet to be determined. For example, breakdown of the materials when implanted is unknown. Soybean oil has the added problem of being difficult to intraoperatively inject into the containment sac. In the case of hyaluronic acid, the interaction of the filler material with the containment sac is not established.

In addition, in U.S. Pat. No. 5,067,965, Ersek, et al., propose a bio-osmotic gel material comprising polyvinylpyrrolidone for use as an implant filler material. However, the materials disclosed by Ersek, et al., are quite expensive and are not capable of injection, thereby requiring filling prior to implantation. As such, the filler materials of Ersek, et al., do not permit modification of the filling procedure following implantation in situations where the initial filling operation proves to be unsatisfactory.

Despite the availability of the foregoing approaches, it will be appreciated that there still exists a need in the art for implant filler materials which are relatively inexpensive, radiolucent, physiologically absorbable, and which have a sufficient viscosity to minimize the risk of deflation. There also exists a need for implant filler materials that can be injected into the physiological shell either before, during, or after the surgical implantation procedure.

SUMMARY OF THE INVENTION

The aforesaid problems are solved, in accordance with the present invention, by methods and materials for filling subcutaneous reconstructive prostheses, for example, breast or facial implants, comprising at least one nonionic surfactant such as at least one polyoxyethylene fatty acid ester. Preferably, the nonionic surfactant comprises at least one polysorbate and, most preferably, includes polysorbate 80. Significantly, the nonionic surfactants of the present invention exhibit a moderately high viscosity ranging from approximately 250–300 centistokes to approximately 500 centistokes at a temperature of approximately 25 degrees centigrade, which is typically the temperature during manufacture.

Polysorbates are a group of fatty acid esters of sorbitol and its anhydrides copolymerized with approximately 20 moles of ethylene oxide for each mole of sorbitol and its anhydrides. Polysorbates are hydrophilic nonionic surfactants which are used as emulsifying agents for the preparation of stable oil-in-water emulsions in pharmaceutical products; they are frequently used with a sorbitan ester in varying proportions to produce products with a range of texture and consistency. They have been used in the formulation of insecticide and herbicide sprays, industrial detergents, cosmetic products, and as emulsifiers in the food industry. They are also used as solubilizing agents for a variety of substances including essential oils and oil-soluble vitamins such as vitamins A, D, and E, and as wetting agents in the formulation of oral and parenteral suspensions. An estimated acceptable daily intake of polysorbates 20, 40, 60, 65, and 80 is up to 25 mg per kilogram of body weight as total polysorbate esters.

Advantageously, the nonionic surfactant implant fillers under the present invention are safe and biodegradable in the event of leakage into surrounding tissues. If filler material escapes from the containment sac, the material is physiologically broken down by normal metabolic processes without inflammatory tissue reaction. The filler materials of the present invention are also radiolucent, thereby permitting facile detection of underlying malignancies or masses with radiologic imaging such as mammograms. Because of the moderately high viscosity of the nonionic surfactants as compared to saline, the fillers of the present invention are less apt to deflate or to develop ripples or fold flaws. The moderately high viscosity of the fillers also results in a more natural appearance and "feel" that substantially mimics the appearance and feel of normal breast tissue. In addition, the fillers of the present invention are injectable, for example, through a peripheral injection port, into one or more lumens of the prosthesis either before, during or even after surgical implantation. The filler materials of the present invention also have a documented history of clinical use in topical, oral, and parenteral forms of human administration. The fillers of the present invention are capable of being mixed with water which creates the potential for varying ratios of polysorbate-water filler materials.

The present invention will be more fully understood upon reading the following detailed description of the preferred embodiment.

DETAILED DESCRIPTION OF THE PREFERRED EMBODIMENT(S)

The following portion of the specification sets forth the preferred embodiments of the present invention. The embodiments of the invention disclosed herein includes the best mode contemplated by the inventor for carrying out the invention in a commercial environment, although it should be understood that various modifications can be accomplished within the parameters of the present invention.

The present invention provides methods and compositions for filling physiological shells, also known as "containment sacs", of prostheses used in subcutaneous implantation such as implants used in breast reconstruction or augmentation. The containment sacs of the prostheses are typically formed from a thin, silicone elastomer envelope. One of ordinary skill in the art will appreciate that the containment sac can include a combination of an inner, less permeable layer and an outer layer in order to minimize leakage of the filler materials. The containment sac of the present invention preferably includes a peripheral injection port in order to permit injection of the filler material as described in more detail hereinbelow. The filler materials of the present invention are compatible with containment sacs having one lumen or with dual chamber containment sacs having more than one lumen, and can therefore be injected into one or more peripheral injection ports. Current commercial sources for known silastic containment sacs and peripheral ports include the Mentor Corporation of Santa Barbara, Calif. and McGhan Medical Corporation of Santa Barbara, Calif.

Significantly, the fillers of the present invention comprise nonionic surfactants that display a moderately high viscosity ranging from approximately 250 centistokes to approximately 500 centistokes, more preferably, 300 centistokes to approximately 500 centistokes, at 25 degrees centigrade. The moderately high viscosity of the fillers permits the fillers to lubricate or coat the inside surface of the containment sac, thereby attenuating the rates of failure due to spontaneous deflation. The moderately high viscosity of the fillers also reduces the incidence of ripples and the development of fold flaws. In addition, the moderately high viscosity enhances the "feel" of the implant, thereby achieving, for example, a breast implant that substantially mimics the "feel" of normal breast tissue. Further, the fillers are radiolucent and permit mammographic inspection for malignancies, and do not hinder early detection of cancer or other abnormalities in adjacent tissue.

In one aspect of the present invention, the nonionic surfactants preferably comprise at least one polyoxyethylene fatty acid ester, which includes a group of nonionic surfactants known as "polysorbates." Polysorbates are emulsifying agents that are used in the pharmaceutical industry as emulsifiers and dispersing agents in medical products and as defoamers and emulsifiers in foods, as well as in cosmetics and skin care products. One of ordinary skill in the art will appreciate that polysorbates are obtained by esterification of sorbitol with one or three molecules of a fatty acid, such as stearic, lauric, oleic, or palmitic acids, under conditions that result in splitting out water from the sorbitol, leaving sorbitan. Approximately 20 moles of ethylene oxide per mole of sorbitol is used in the condensation.

Commercially available compounds include: Polysorbate 20, Polysorbate 40, Polysorbate 60, Polysorbate 65, Polysorbate 80, and Polysorbate 85. Of these, Polysorbate 80 has shown the best physical properties being an oily liquid that is miscible with water. However, nonionic surfactants represent a family of compounds of which polysorbates are but one example. Other nonionic surfactants may be utilized if they possess the aforementioned physical properties to function as implant fillers under the present invention.

The filler materials of the present invention most preferably include polysorbate 80 [polyoxyethylene (20) sorbitan monoleate], in which the fatty acid is oleate. Polysorbate 80 has a desirable viscosity ranging from 270–430 centistokes and has a pH between 5 and 7 in a 5% aqueous solution. However, other nonionic surfactants can be employed, including other polysorbates, such as polysorbate 20 [polyoxyethylene (20) sorbitan monolaureate], polysorbate 60 [polyoxyethylene (20) sorbitan monostearate] and polysorbate 65 [polyoxyethylene (20) sorbitan tristearate].

Critically, the nonionic nature of the surfactants included in the fillers of the present invention is important because the material lacks polarity with its constituent elements. Ionic surfactants are undesirable because they are fairly irritating to human tissue, some of which may even be toxic. It is to be noted that the nonionic surfactants of the present invention can be used as a unitary filler material, or alternatively, in combination with other filler materials. Other suitable materials that can be included with the nonionic surfactants include, but are not limited to, water, saline, triglycerides, hyaluronic acid, hydrogels, or combinations thereof.

The nonionic surfactant fillers of the present invention are safe and biodegradable inasmuch as they are physiologically absorbed in the event of leakage from the containment sac into surrounding or other body tissues. By way of example, polysorbates are metabolically broken down in the body wherein the fatty acid moiety is hydrolyzed from the polyoxyethylene moiety and oxidized like other fatty acids. Meanwhile, although the polyoxyethylene moiety is not metabolized further in the body, it is safely excreted. As a result, the nonionic surfactant filler materials of the present invention are nontoxic when implanted in body tissues.

The nonionic surfactant fillers of the present invention are advantageously injectable. In order to permit injection, the containment sac is provided with a peripheral injection port which is adapted to permit flow of liquid filler materials therethrough. The containment sacs are typically formed of flexible, elastomeric envelopes that are adapted to be surgically implanted while retaining a desired shape when filled with a filling material. Known containment sacs and injection ports are described, for example, in U.S. Pat. Nos. 4,731,081; 4,775,379; and 5,658,329. The filler can be injected prior to, during or subsequent to the surgical implantation procedure, as desired. The injectability of the fillers of the present invention enhance flexibility for modifying the implantation results after an initial filling procedure.

In order to promote a further understanding and appreciation of the present invention and its attendant advantages, the following Examples are provided. It will be understood that these Examples are illustrative and not limiting in nature.

EXAMPLE 1 (BACKGROUND)-BIOMATERIAL BIOCOMPATIBILITY (1994)

As previously published (Eppley et al.: A Potential New Biomaterial Composite for Dermal Augmentation, *Annals of Plastic Surgery* 32:463, 1995), polysorbate (Tween 80) was evaluated as a carrier vehicle for a subcutaneously injected charged bead material. No immediate (24 to 48 hour) inflammatory response was seen in a superficial skin site. At time periods of up to one year after implantation, a histologic response around the bead implants similar to that when this carrier vehicle was not used was seen. This study demonstrated the biocompatibility in mammalian tissues of polysorbate 80 and its complete absorption and elimination without adverse effects shortly after injection.

EXAMPLE 2-IMPLANT LEAKAGE (1990–95)

A five year in vitro evaluation of polysorbate 80 filled tissue expanders, i e., containment sacs (5 cc), was undertaken to evaluate the interaction of the filler material on the surrounding shelf. After five years of implantation ex vivo, no adverse effects on the silicone shell were observed including a notable lack of filler material bleed (unlike silicone gel), no overt disruption of the implant shell, and no apparent loss of implant shell elasticity when under maximal compression (touching of the sidewalls).

EXAMPLE 3-IN VITRO CONTAINMENT SAC STUDY

Polysorbate 80 was instilled into sample breast implants (Mentor Company) and allowed to "sit-on-the-shelf" for two years. This study demonstrated that the filler material could be injected into the containment sac using conventional methods. Once filled, they exhibited an excellent palpability (similar to silicone gel). Over the shelf test, no breakdown of the containment sac was seen nor did any "bleed" of filler material occur. In this regard, there was no expression of filler material on the outside of the containment sac as is commonly seen with silicone gel.

EXAMPLE 4-IN VIVO IMPLANTATION

Small-sized (5 cc) tissue expanders (McGhan Company) were instilled with polysorbate 80 and implanted in the subcutaneous location in the backs of New Zealand rabbits. Time of implantation was 6 months in 5 animals. Retrieval histologic analysis demonstrated a typical collagenous capsule surrounding the implants without evidence of material extrusion, acute or chronic inflammatory reaction, or abnormal thickening of the capsule.

While the preferred embodiment of the invention has been disclosed, it should be appreciated that the invention is susceptible of modification without departing from the spirit of the invention or the scope of the subjoined claims.

What is claimed is:

1. A filler composition for a physiological shell situated subcutaneously, the composition having a viscosity ranging from approximately 250 centistokes to approximately 500 centistokes at approximately 25° C., and comprising at least one nonionic surfactant as a filler.

2. A composition as defined in claim 1 wherein the nonionic surfactant comprises at least one polyoxyethylene sorbate ester derivative.

3. A composition as defined in claim 1 wherein the nonionic surfactant is selected from the group consisting of: polysorbate 20, polysorbate 40, polysorbate 60, polysorbate 65, polysorbate 80, polysorbate 85, or combinations thereof.

4. A composition as defined in claim 1 further comprising at least one additive selected from the group consisting of water, saline, triglycerides, hyaluronic acid, hydrogels, or any combination thereof.

5. A composition as defined in claim 1 wherein said composition is included in a physiological shell adapted for use in a breast implant.

6. A composition as defined in claim 1 wherein the filler is utilized with shells having one lumen.

7. A composition as defined in claim 1 wherein the filler is utilized with shells having more than one lumen.

8. A composition as defined in claim 1 wherein the filler comprises polysorbate 80.

9. A method for filling a physiological shell used in mammalian soft tissue implants comprising the steps of:
providing at least one injectable port on the shell;
injecting a filler composition through said port(s) into said shell, the composition having a viscosity ranging from approximately 250 centistokes to approximately 500 centistokes at approximately 25° C. and comprising at least one nonionic surfactant as a filler.

10. A method as defined in claim 9 wherein the filler composition is injected into the physiological shell prior to implanting said physiological shell subcutaneously.

11. A method as defined in claim 9 wherein the filler composition is injected into the physiological shell during implantation of said physiological shell subcutaneously.

12. A method as defined in claim 9 wherein the filler composition is injected into the physiological shell after implanting said physiological shell subcutaneously.

13. A method as defined in claim 9 wherein the nonionic surfactant comprises at least one derivative of a polyoxyethylene sorbate ester.

14. A method as defined in claim 9 wherein the nonionic surfactant is selected from polysorbate 20, polysorbate 40, polysorbate 60, polysorbate 65, polysorbate 80, polysorbate 85 and combinations thereof.

15. A method as defined in claim 9 wherein the composition further comprises at least one additive selected from the group consisting of water, saline, triglycerides, hyaluronic acid, hydrogels, or any combination thereof.

16. A method as defined in claim 9 wherein the shell includes one lumen such that the at least one injectable port is in communication with the one lumen so as to permit filling of the one lumen via the at least one injectable port, and wherein the filler composition is injected into the one lumen of said shell.

17. A method as defined in claim 9 wherein the shell includes two lumens such that each of said two lumens is in communication with at least one of the ports so as to permit filling of the two lumens via the at least one injectable port, and wherein the filler composition is injected into the two lumens of said shell.

18. A method as defined in claim 9 wherein the composition comprises polysorbate 80.

19. An implantable soft tissue prosthesis comprising:
a hollow shell formed of a flexible envelope having at least one lumen and at least one injection port; and
a material for filling the lumen(s) through the injection port(s), the material comprising at least one nonionic surfactant as a filler and having a viscosity ranging from approximately 250 centistokes to approximately 500 centistokes at approximately 25° C., said prosthesis capable of being surgically implanted.

20. An implantable soft tissue prosthesis as defined in claim 19 wherein the nonionic surfactant is selected from the group consisting of: polysorbate 20, polysorbate 40, polysorbate 60, polysorbate 65, polysorbate 80, polysorbate 85, or combinations thereof.

21. A method for implanting a physiological shell used in mammalian soft tissue implants, said method comprising the steps of:
providing at least one injectable port on the shell;
injecting a filler composition through said port(s) into said shell, the composition having a viscosity ranging from approximately 250 centistokes to approximately 500 centistokes at approximately 25° C. and comprising at least one nonionic surfactant as a filler; and
implanting said physiological shell subcutaneously.

22. A filler composition for a physiological shell capable of being situated subcutaneously, the composition having a viscosity ranging from approximately 250 centistokes to approximately 500 centistokes at approximately 25° C., and consisting essentially of at least one nonionic surfactant as a filler.

* * * * *